United States Patent
Kim et al.

(10) Patent No.: US 10,478,286 B2
(45) Date of Patent: Nov. 19, 2019

(54) ARTIFICIAL VESTIBULAR ORGAN SYSTEM

(71) Applicant: INHA UNIVERSITY RESEARCH AND BUSINESS FOUNDATION, Incheon (KR)

(72) Inventors: Kyu Sung Kim, Seoul (KR); Hyeon Min Shim, Incheon (KR); Sangmin Lee, Incheon (KR); Woo Key Lee, Gunpo-si (KR); Bong Sup Shim, Incheon (KR); Ki Hwan Hong, Seoul (KR); Soon Hyoung Park, Seoul (KR)

(73) Assignee: INHA UNIVERSITY RESEARCH AND BUSINESS FOUNDATION, Incheon (KR)

( * ) Notice: Subject to any disclaimer, the term of this patent is extended or adjusted under 35 U.S.C. 154(b) by 0 days.

(21) Appl. No.: 15/474,224

(22) PCT Filed: Sep. 30, 2015

(86) PCT No.: PCT/KR2015/010286
§ 371 (c)(1),
(2) Date: Mar. 30, 2017

(87) PCT Pub. No.: WO2016/072621
PCT Pub. Date: May 12, 2016

(65) Prior Publication Data
US 2018/0168801 A1    Jun. 21, 2018

(30) Foreign Application Priority Data

Nov. 7, 2014 (KR) .......................... 10-2014-0154154

(51) Int. Cl.
*A61F 2/18* (2006.01)
*A61N 1/00* (2006.01)
(Continued)

(52) U.S. Cl.
CPC .................. *A61F 2/18* (2013.01); *A61N 1/00* (2013.01); *A61N 1/0526* (2013.01);
(Continued)

(58) Field of Classification Search
CPC ................................... A61F 2/18; A61F 11/04
See application file for complete search history.

(56) References Cited

U.S. PATENT DOCUMENTS 8,843,204 B2   9/2014 Garnham et al.
2007/0255154 A1   11/2007 Lu et al.
(Continued)

FOREIGN PATENT DOCUMENTS

JP   62-35266 A    2/1987
JP   4679464 B2    2/2011
KR   10-2012-0125568 A    11/2012

OTHER PUBLICATIONS

Japanese Office Action dated Oct. 17, 2017 in corresponding Japanese Patent Application No. 2017-514244 (2 pages in Japanese).
(Continued)

*Primary Examiner* — Yashita Sharma
(74) *Attorney, Agent, or Firm* — NSIP Law

(57) ABSTRACT

An artificial vestibular organ system includes an artificial semicircular canal; a liquid filled in the artificial semicircular canal; artificial hair for sensing movement of liquid in the artificial semicircular canal; a signal conversion unit for converting an electrical or magnetic signal generated from the artificial hair into a body stimulation signal; a body stimulation pulse generation unit for transmitting the body stimulation pulse converted by the signal conversion unit to the ampulla; and a power unit. The artificial hair can be constituted in a pressure sensing manner or in a speed sensing manner for sensing the flow rate. The pressure
(Continued)

sensing type can be formed of flex sensor, a piezoelectric sensor, or an FSR sensor, and the velocity sensing type can include rotary wings rotated according to the flow of the liquid or a speed measuring instrument for measuring the rotating speed of the rotary wings.

9 Claims, 5 Drawing Sheets

(51) Int. Cl.
    *A61N 1/05*     (2006.01)
    *A61N 1/36*     (2006.01)
    *A61F 11/04*     (2006.01)
(52) U.S. Cl.
    CPC ....... *A61N 1/3606* (2013.01); *A61N 1/36128* (2013.01); *A61F 11/04* (2013.01); *A61F 2002/183* (2013.01)

(56) References Cited

U.S. PATENT DOCUMENTS

| | | |
|---|---|---|
| 2012/0000474 A1 | 1/2012 | Merfeld et al. |
| 2012/0277835 A1 | 11/2012 | Della Santina et al. |
| 2014/0194673 A1 | 7/2014 | Goldenberg et al. |
| 2016/0089571 A1* | 3/2016 | Wesley ................ A61B 5/1071 482/8 |

OTHER PUBLICATIONS

Ahn, Joong, Ho. "Development of Mulitchannel Vestibular Prosthesis for Treatment of Bilateral Vestibular Deficiency." Korean Journal of Otorhinolaryngology—Head and Neck Surgery 56.1 (2013): 1-6.

* cited by examiner

ARTIFICIAL VESTIBULAR ORGAN SYSTEM

CROSS REFERENCE TO RELATED APPLICATIONS

This application is a continuation of International Application No. PCT/KR2015/010286, filed on Sep. 30, 2015, which claims the benefit of priority from Korean Application No. 10-2014-0154154, filed on Nov. 7, 2014, in the Korean Intellectual Property Office, the entire disclosures of each of which are incorporated herein by reference for all purposes.

ACKNOWLEDGEMENTS

This research was supported by Basic Science Research Program through the National Research Foundation of Korea (NRF) funded by the Ministry of Education (2010-0020163).

FIELD

The following description relates to an artificial vestibular organ system that is applied to the body of a person having a damaged vestibular organ so as to act as a semicircular canal.

DESCRIPTION OF RELATED ART

A vestibular organ is located in an inner ear placed in the innermost of an ear and serves body balance. The vestibular organ includes the vestibule having the saccule and the utricle and serving to detect equilibrium and the three semicircular canals serving to detect rotational movements.

The otoliths are located on the cilia of the macula of the vestibule, and if a human body is tilted or takes an accelerated motion, the cilia recognize the movements of the otoliths and sense them.

The three semicircular canals detect rotational movements and are classified into superior, lateral, and posterior semicircular canals according to their position. The three semicircular canals are located on three planes of a space in such a manner as to be perpendicular to each other.

The lymph is filled in each semicircular canal, and hair cells in the semicircular canal sense the movement of the lymph to recognize the rotational movement.

If a head is tilted or a body moves, the otoliths of the vestibule are inclined, and the weight of the otoliths stimulates the hair cells to allow the cerebellum to detect a sense of position.

That is, the vestibule serves to sense gravity or three-dimensional linear acceleration motion, and the three semicircular canals serves to sense the rotation of the body according to the movement of the lymph.

If the vestibular organ becomes disabled, however, it does not sense equilibrium and rotational motions, thereby making it impossible to take normal activities, and therefore, there is a definite need for the development of an artificial vestibular organ capable of acting as the disabled vestibular organ.

DISCLOSURE

Technical Problem

Accordingly, the present description has been made in view of the above-mentioned problems occurring in the prior art, and it is an object of the present description to provide an artificial vestibular organ system that is applied to a body of a person having a damaged vestibular organ so as to act as a semicircular canal and hair cells.

Technical Solution

To accomplish the above-mentioned object, according to an embodiment of the present disclosure, there is provided an artificial vestibular organ system including: an artificial semicircular canal; a liquid filled in the artificial semicircular canal; artificial hair for sensing the movement of the liquid in the artificial semicircular canal; a signal conversion unit for converting an electrical or magnetic signal generated from the artificial hair into a body stimulation signal; a body stimulation pulse generation unit for converting the body stimulation signal provided from the signal conversion unit into a body stimulation pulse to transmit the body stimulation signal to the ampulla; and a power unit for supplying power to the artificial hair, the signal conversion unit and the body stimulation pulse generation unit.

According to the embodiment, the artificial hair is formed of pressure sensing type artificial hair for sensing a movement pressure of the liquid.

According to the embodiment, the pressure sensing type artificial hair includes a flex sensor using a bending element, a piezoelectric sensor using a piezoelectric element, or an FSR (force sensing resistor) sensor using a polymer film element.

According to the embodiment, the artificial hair is formed of speed sensing type artificial hair for sensing a flow rate of the liquid according to the movement of the liquid.

According to the embodiment, the speed sensing type artificial hair includes rotary wings rotated by the movement of the liquid and a speed measuring instrument for measuring the rotating speed of the rotary wings.

According to the embodiment, the speed measuring instrument is formed of a hall sensor or optical encoder.

Advantageous Effects

According to an embodiment of the present disclosure, the artificial vestibular organ system is applied to the body of a person having a damaged vestibular organ so as to act as a semicircular canal, thereby assisting the rehabilitation for people experiencing difficulties due to their damaged vestibular organ.

DETAILED DESCRIPTION

Hereinafter, an explanation on a structure of an artificial vestibular organ system according to the present description will be in detail given with reference to the attached drawing.

Figure 1:
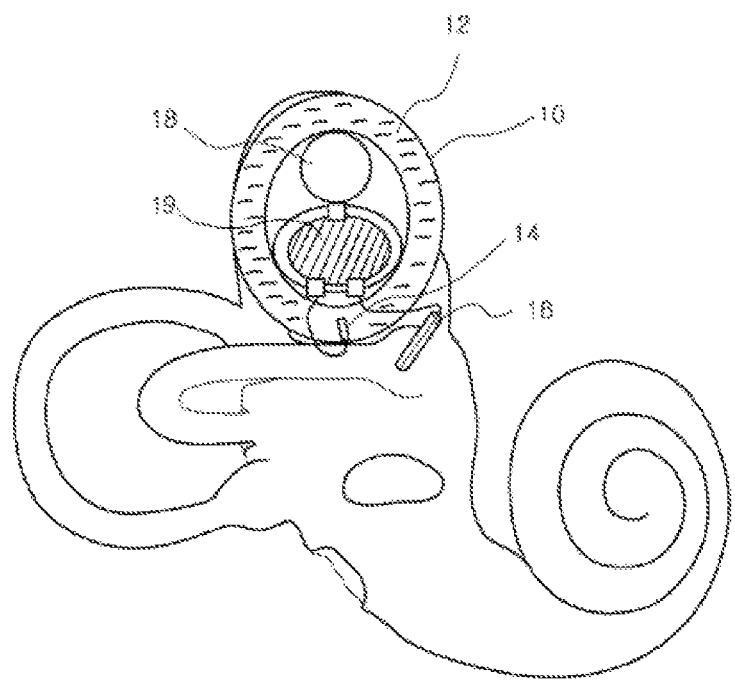
FIG. 1 is a schematic view showing an embodiment of an artificial vestibular organ system according to the present disclosure.

FIG. 1 is a schematic view showing an embodiment of an artificial vestibular organ system according to the present description.

Referring to FIG. 1, an artificial vestibular organ system according to the present description includes an artificial semicircular canal 10, a liquid 12 filled in the artificial semicircular canal 10, artificial hair 14 for sensing the movement of the liquid 12 in the artificial semicircular canal 10 to generate an electrical or magnetic signal corresponding to the sensed result, a signal conversion unit 19 for converting the electrical or magnetic signal generated from the artificial hair 14 into a body stimulation signal, a body stimulation pulse generation unit 16 for converting the body stimulation signal provided from the signal conversion unit 19 into a body stimulation pulse to transmit the body stimulation signal to the ampulla, and a power unit 18 for supplying power to the artificial hair 14, the signal conversion unit 19 and the body stimulation pulse generation unit 16. The artificial vestibular organ system may be implanted into the body of a person having a damaged vestibular organ.

Figure 2A:
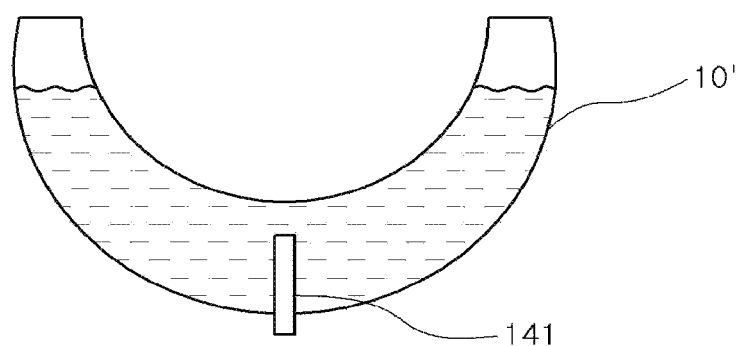
FIG. 2A is a schematic view showing an embodiment of a pressure sensing type artificial hair adopted in the artificial vestibular organ system.
Figure 2B:
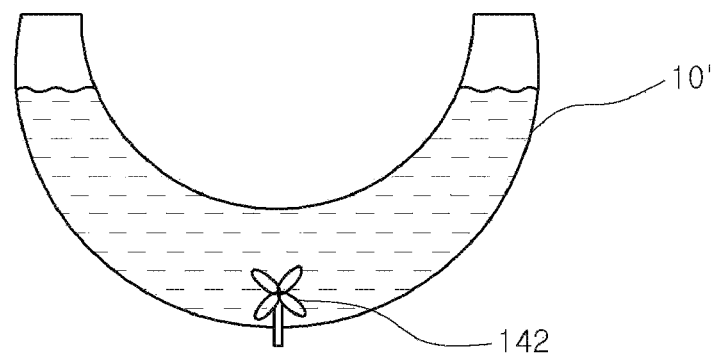
FIG. 2B is a schematic view showing an embodiment of a speed sensing type artificial hair adopted in the artificial vestibular organ system.

The artificial semicircular canal 10 has a shape of a closed type tube, and as shown in FIG. 1, it has a shape of a circular tube. Further, as shown in FIGS. 2A and 2B, the artificial semicircular canal 10 has a shape of a semicircular tube.

The liquid 12 filled in the artificial semicircular canal 10 is artificial lymph.

The body stimulation pulse generation unit 16 is formed of a vestibular nerve stimulation electrode.

The artificial hair 14 senses the movement of the liquid 12 in the artificial semicircular canal 10, generates the electrical or magnetic signal according to the movement of the liquid 12, and outputs the signal to the signal conversion unit 19. The artificial hair 14 is formed of pressure sensing type artificial hair in which the pressure generated by the movement of the liquid 12 is sensed to generate and output the electrical or magnetic signal according to the sensed pressure of the liquid 12, and otherwise, the artificial hair 14 is formed of speed sensing type artificial hair in which the flow rate generated by the movement of the liquid 12 is sensed to generate and output the electrical or magnetic signal according to the sensed flow rate of the liquid 12.

The pressure sensing type artificial hair 14 includes one of various sensors capable of sensing the pressure generated by the movement of the liquid 12, such as a flex sensor, a piezoelectric sensor, a force sensing resistor (FSR) sensor and so on.

FIG. 2A is a schematic view showing the pressure sensing type artificial hair adopted in an artificial vestibular organ system according to the present description, wherein a flex sensor is adopted as the artificial hair. Referring to FIG. 2A, the flex sensor has a bending element 141 from which deformation or bending is generated through an external pressure, and resistance values of the bending element 141 are changed in accordance with the deformed degree of the bending element 141, thereby allowing changes in the pressure generated by the movement of the liquid 12.

The flex sensor is applied to both of the artificial semicircular canal 10 having the shape of the circle as shown in FIG. 1 and the artificial semicircular canal 10' having the shape of the semicircle as shown in FIG. 2A.

The piezoelectric sensor measures changes in pressure by utilizing a piezoelectric element that generates mechanical deformation when an electric charge is generated in a crystal to which a pressure is applied or when an electric field is applied to the crystal.

The FSR sensor measures changes in pressure by utilizing a polymer film element that is reduced in resistance as pressure is applied thereto. In this case, a Wheatstone Bridge is utilized to convert the changes in the resistance value of the FSR sensor into an electrical signal.

FIG. 2B is a schematic view showing an embodiment of the speed sensing type artificial hair adopted in the artificial vestibular organ system. Referring to FIG. 2B, the speed sensing type artificial hair includes rotary wings 142 rotated by the movement of the liquid 12 and a speed measuring instrument for measuring the rotating speed of the rotary wings 142. As shown in FIG. 2B, the rotary wings 142 may comprise blades that rotate about a central axis. In this case, the speed measuring instrument is formed of a hall sensor or optical encoder.

Under the above-mentioned structure, now, an explanation on the operation of the artificial vestibular organ system according to the present description will be in detail given.

If a human body takes a rotational motion, first, the liquid 12 filled in the artificial semicircular canal 10 becomes move, and the artificial hair 14 responds to the movement of the liquid 12 and thus generates an electrical signal.

If the pressure sensing type artificial hair 14 is provided, the movement pressure of the liquid 12 is measured according to the characteristics of the sensor used for sensing the pressure, and according to the sensed result, next, the electrical signal is generated. As mentioned above, the pressure sensing type artificial hair 14 is one selected from the flex sensor, piezoelectric sensor, and FSR sensor.

Figure 3:
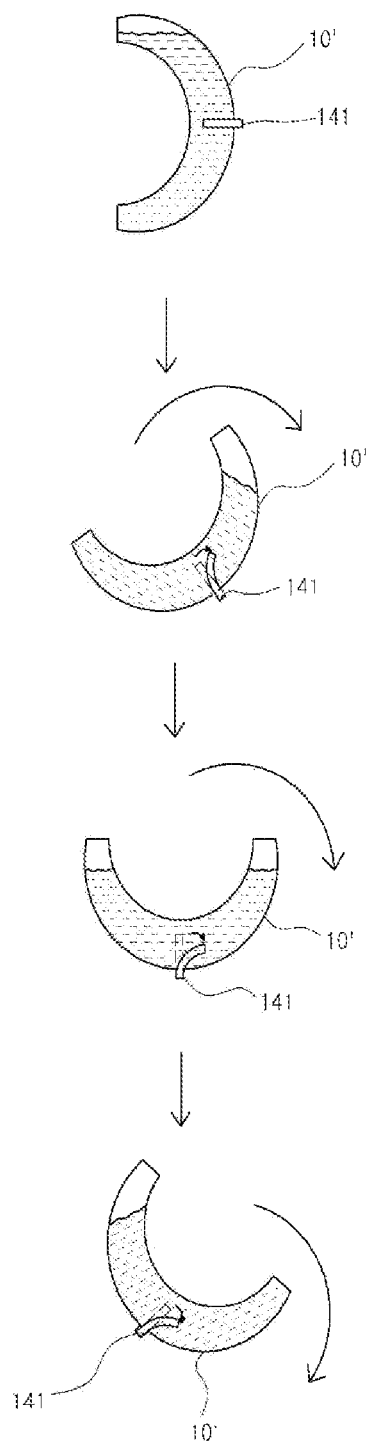
FIG. 3 is an exemplary view showing operating processes of the pressure sensing type artificial hair adopted in the artificial vestibular organ system.

FIG. 3 is a view showing operating processes of the pressure sensing type artificial hair adopted in an embodiment of the artificial vestibular organ system according to the present description, wherein the flex sensor is selected as the artificial hair 14. In this case, as shown in FIG. 3, if the artificial semicircular canal 10' rotates, the liquid 12 moves according to the rotation of the artificial semicircular canal 10', and under the movement of the liquid 12, the bending element 141 is inclined toward the moving direction of the liquid 12, that is, toward the relative rotational direction to the rotation of the artificial semicircular canal 10'. As the inclination of the bending element 141 is generated according to the rotation of the artificial semicircular canal 10', accordingly, the resistance values of the bending element 141 are changed in accordance with the deformed degree of the bending element 141, thereby allowing changes in the movement pressure of the liquid 12 to be measured.

On the other hand, as shown in FIG. 2B, if the speed sensing type artificial hair 14, which has the rotary wings 142 and the speed measuring instrument, is provided, the rotary wings 142 rotate by the movement of the liquid 12, and the speed measuring instrument senses the movement speed of the rotary wings 142 and generates and outputs an electrical signal corresponding to the sensed speed. As mentioned above, the speed measuring instrument is formed of a hall sensor or optical encoder.

Next, the signal conversion unit 19 converts the electrical signal generated from the artificial hair 14 into a body stimulation signal and transmits the body stimulation signal to the body stimulation pulse generation unit 16. The body stimulation pulse generation unit 16, which is formed of the vestibular nerve stimulation electrode, converts the body stimulation signal provided from the signal conversion unit 19 into the body stimulation pulse and transmits the body stimulation pulse to the ampulla. As a result, the human body senses his or her rotational motion through the body stimulation pulse transmitted to the ampulla.

According to the present description, on the other hand, if the electrical signal generated from the artificial hair 14 is weak, the artificial vestibular organ system further includes a signal amplification unit for amplifying the electrical signal. The signal amplification unit is formed of an inverting amplifier, a noninverting amplifier, or an instrumentation amplifier. The signal amplification unit is connected to an output terminal of the artificial hair 14 or an output terminal of the signal conversion unit 19.

The body stimulation pulse generation unit 16 determines a firing rate of a nerve according to the body stimulation signal received from the signal conversion unit 19 and generates and outputs a pulse signal of a frequency corresponding to the firing rate. The body stimulation pulse generation unit 16 is formed of a voltage controlled oscillator VCO.

According to the present description, on the other hand, if the bending element 141 is provided to have triboelectric charging, it can be operated, without any separate power supply. In this case, the triboelectric charging makes use of the electricity generated by the friction between metal objects.

Figure 4A:
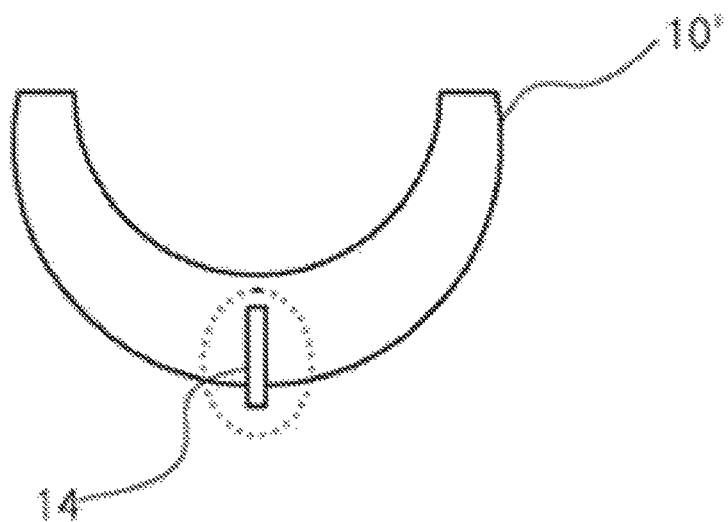
FIGS. 4A to 4C are views showing an embodiment of a triboelectric charging type artificial hair adopted in the artificial vestibular organ system.
Figure 4B:
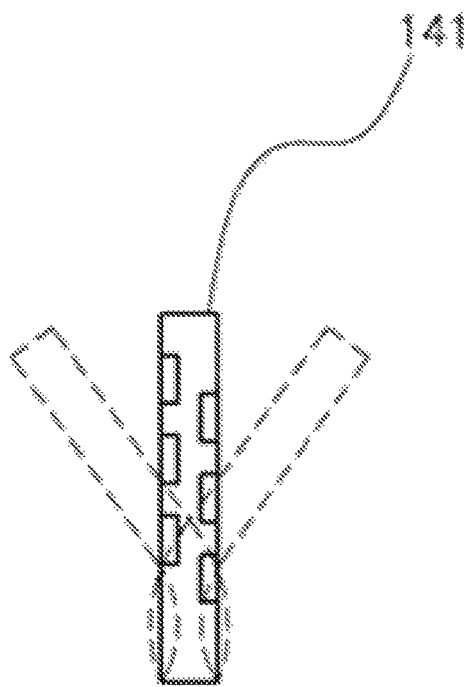
Figure 4C:
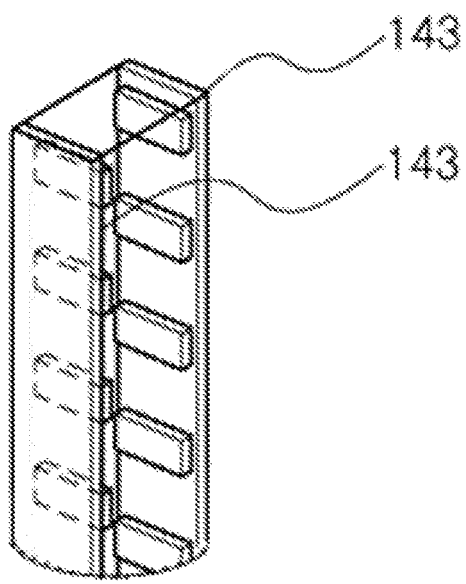

FIGS. 4A to 4C are views showing the triboelectric charging type bending element used as the artificial hair of the artificial vestibular organ system according to the present description. Referring to FIGS. 4A to 4C, the triboelectric charging type bending element 141 is configured wherein a pair of metal members 143 is arranged in such a manner as to be contactable with each other, and through the movements of the metal members 143, the metal members 143 become frictional to each other to generate electricity, so that the generated electricity is used as power. If the human body moves, that is, the bending element 141 moves according to the movement of the liquid 12 filled in the artificial semicircular canal 10', and accordingly, the metal members 143 located inside the bending element 141 are frictional to each other.

According to the present description, the bending element 141 can be operated at low power in the human body, and accordingly, the triboelectric charging type bending element 141 can be adopted very properly.

On the other hand, the artificial vestibular organ system according to the present description can be applied to three axes, that is, pitch, yaw and roll axes, respectively, so that three artificial vestibular organ systems are located in the three semicircular canals. If the three artificial vestibular organ systems according to the present description are located inside the three semicircular canals, the human body can recognize all directions.

While the present description has been described with reference to the particular illustrative embodiments, it is not to be restricted by the embodiments but only by the appended claims. It is to be appreciated that those skilled in the art can change or modify the embodiments without departing from the scope and spirit of the present description.

The artificial vestibular organ system according to the present description may be widely applied for use in a medical field.

The signal conversion unit 19, power unit 18 and body stimulation pulse generating unit 16 and other components illustrated in FIGS. 1 to 4 are implemented with hardware components. The hardware components may include controllers, generators, non-transitory memories, processors, transducer, and any other electronic components known to one of ordinary skill in the art.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An artificial vestibular organ system comprising: an artificial semicircular canal;
   an artificial hair in the artificial semicircular canal configured to generate an electrical or magnetic signal according to changes in position; and
   a body stimulation pulse generation unit configured to generate a body stimulation pulse using the electrical or magnetic signal generated from the artificial hair to transmit the body stimulation pulse to an ampulla,
   wherein the artificial hair is disposed on one surface of an interior of the artificial semicircular canal and is configured to sense a movement of a liquid.

2. The artificial vestibular organ system according to claim 1, further comprising a power unit configured to supply power to the artificial hair and the body stimulation pulse generation unit.

3. The artificial vestibular organ system according to claim 1, wherein the artificial hair comprises a pressure sensing type artificial hair for sensing a pressure according to the movement of the liquid.

4. The artificial vestibular organ system according to claim 3, wherein the pressure sensing type artificial hair comprises a triboelectric sensor using triboelectric charging.

5. The artificial vestibular organ system according to claim 3, wherein the pressure sensing type artificial hair comprises a flex sensor.

6. The artificial vestibular organ system according to claim 3, wherein the pressure sensing type artificial hair comprises a piezoelectric sensor.

7. The artificial vestibular organ system according to claim 3, wherein the pressure sensing type artificial hair comprises a force sensing resistor (FSR) sensor.

8. The artificial vestibular organ system according to claim 1, wherein three artificial vestibular organ systems are located at three different axes to recognize all directions.

9. The artificial vestibular organ system according to claim 8, wherein the three different axes are pitch, yaw and roll axes.

* * * * *